(12) United States Patent
Schneider et al.

(10) Patent No.: US 12,370,091 B2
(45) Date of Patent: Jul. 29, 2025

(54) METHODS AND APPARATUSES FOR MAKING ABSORBENT ARTICLES HAVING CONTOURED BELTS

(71) Applicant: The Procter & Gamble Company, Cincinnati, OH (US)

(72) Inventors: Uwe Schneider, Cincinnati, OH (US); Michael Devin Long, Springfield, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 18/130,951

(22) Filed: Apr. 5, 2023

(65) Prior Publication Data
US 2023/0240902 A1 Aug. 3, 2023

Related U.S. Application Data

(60) Continuation of application No. 16/129,852, filed on Sep. 13, 2018, now Pat. No. 11,648,155, which is a
(Continued)

(51) Int. Cl.
*A61F 13/15* (2006.01)
*A61F 13/496* (2006.01)
*B31D 1/00* (2017.01)

(52) U.S. Cl.
CPC .... *A61F 13/1565* (2013.01); *A61F 13/15723* (2013.01); *A61F 13/15739* (2013.01);
(Continued)

(58) Field of Classification Search
CPC ............ A61F 13/1565; A61F 13/15723; A61F 13/15739; A61F 13/15747;
(Continued)

(56) References Cited

U.S. PATENT DOCUMENTS 3,860,003 A  1/1975  Buell
4,216,687 A  8/1980  Dickover et al.
(Continued)

FOREIGN PATENT DOCUMENTS

EP  1574191 A1  9/2005
JP  2010029278 A  2/2010
(Continued)

OTHER PUBLICATIONS

All Office Actions; U.S. Appl. No. 14/559,942 filed on Dec. 4, 2014.
(Continued)

*Primary Examiner* — Sameh Tawfik
(74) *Attorney, Agent, or Firm* — Charles R. Matson

(57) ABSTRACT

The present disclosure relates to methods and apparatuses for assembling disposable pant diapers having contoured elastic belts. During the assembly process, opposing end regions of chassis are connected with the elastic belts in the form of first and second continuous elastic laminates. The chassis are then folded to place the elastic laminates into a facing relationship. The inner longitudinal edges of one or both the elastic laminates are then cut to define a contoured shape. Discrete pieces of trim material may be removed from one or both the elastic laminates, and the first and second continuous elastic laminates are cut in the cross direction to form discrete pant diapers. In some configurations, a single knife both removes the trim material and cuts the elastic laminates in cross direction. And in some configurations, a first knife removes the trim material and a second knife cuts the elastic laminates in cross direction.

9 Claims, 13 Drawing Sheets

Related U.S. Application Data division of application No. 14/559,942, filed on Dec. 4, 2014, now Pat. No. 10,098,792.

(60) Provisional application No. 61/918,087, filed on Dec. 19, 2013.

(52) U.S. Cl.
CPC .. *A61F 13/15747* (2013.01); *A61F 13/15756* (2013.01); *A61F 13/15804* (2013.01); *A61F 13/496* (2013.01); *B31D 1/0075* (2013.01)

(58) Field of Classification Search
CPC .......... A61F 13/15756; A61F 13/15804; A61F 13/496; B31D 1/0075
USPC .......................................................... 493/374
See application file for complete search history.

(56) References Cited

U.S. PATENT DOCUMENTS

| | | | |
|---|---|---|---|
| 4,578,133 A | 3/1986 | Oshefsky et al. | |
| 4,610,678 A | 9/1986 | Weisman | |
| 4,673,402 A | 6/1987 | VVeisman et al. | |
| 4,695,278 A | 9/1987 | Lawson | |
| 4,704,115 A | 11/1987 | Buell | |
| 4,795,454 A | 1/1989 | Dragoo | |
| 4,834,735 A | 5/1989 | Alemany | |
| 4,888,231 A | 12/1989 | Angstadt | |
| 4,909,803 A | 3/1990 | Aziz | |
| 5,562,646 A | 10/1996 | Goldman | |
| 5,599,335 A | 2/1997 | Goldman | |
| 5,628,097 A | 5/1997 | Benson | |
| 5,669,894 A | 9/1997 | Goldman | |
| 5,916,661 A | 6/1999 | Benson | |
| 6,107,539 A | 8/2000 | Palumbo | |
| 6,279,440 B1 | 8/2001 | Truttmann et al. | |
| 6,545,197 B1 | 4/2003 | Muller | |
| 6,790,798 B1 | 9/2004 | Suzuki | |
| 7,438,779 B2 | 10/2008 | Nakakado | |
| 7,569,039 B2 | 8/2009 | Matsuda | |
| 7,587,966 B2 | 9/2009 | Nakakado | |
| 7,708,857 B2 | 5/2010 | Ukegawa | |
| 7,749,212 B2 | 7/2010 | Wada | |
| 7,971,525 B2 | 7/2011 | Leins | |
| 8,096,931 B2 | 1/2012 | Yamamoto | |
| 8,440,043 B1 | 5/2013 | Schneider | |
| 8,491,741 B2 * | 7/2013 | Beuther | A61F 13/15593 156/229 |
| 8,579,780 B2 | 11/2013 | Senbo | |
| 8,622,983 B2 * | 1/2014 | Wilkes | A61F 13/496 604/385.27 |
| 8,739,670 B2 | 6/2014 | Coulombe | |
| 8,758,543 B2 | 6/2014 | Yagyu et al. | |
| 8,771,449 B2 | 7/2014 | Takino et al. | |
| 9,119,747 B2 | 9/2015 | Knecht | |
| 9,295,588 B2 | 3/2016 | Walsh et al. | |
| 9,301,882 B2 | 4/2016 | Sablone | |
| 9,381,120 B2 | 7/2016 | Bäck et al. | |
| 10,052,238 B2 | 8/2018 | Mukai et al. | |
| 10,098,792 B2 | 10/2018 | Schneider et al. | |
| 2002/0193775 A1 | 12/2002 | Shimoe | |
| 2004/0097895 A1 | 5/2004 | Busam | |
| 2004/0108043 A1 | 6/2004 | Otsubo | |
| 2004/0158212 A1 | 8/2004 | Ponomarenko | |
| 2005/0107764 A1 | 5/2005 | Matsuda | |
| 2006/0244166 A1 | 11/2006 | Wada et al. | |
| 2006/0254708 A1 * | 11/2006 | Wada | A61F 13/15723 156/271 |
| 2006/0266467 A1 | 11/2006 | Mlinar | |
| 2009/0211070 A1 * | 8/2009 | Schneider | B65H 23/025 26/88 |
| 2009/0312730 A1 | 12/2009 | Lavon | |
| 2011/0036217 A1 | 2/2011 | Schneider | |
| 2012/0055613 A1 | 3/2012 | Baeck | |
| 2012/0061015 A1 | 3/2012 | Lavon | |
| 2012/0061016 A1 * | 3/2012 | Lavon | A61F 13/15756 156/226 |
| 2012/0065043 A1 | 3/2012 | Lam et al. | |
| 2012/0152446 A1 | 6/2012 | Rhodes et al. | |
| 2012/0157281 A1 | 6/2012 | Schneider et al. | |
| 2012/0157282 A1 | 6/2012 | Schneider | |
| 2013/0255861 A1 | 10/2013 | Schneider | |
| 2013/0255862 A1 | 10/2013 | Schneider | |
| 2013/0255863 A1 | 10/2013 | Lavon | |
| 2013/0255864 A1 | 10/2013 | Schneider | |
| 2013/0255865 A1 | 10/2013 | Brown | |
| 2013/0296148 A1 | 11/2013 | Schneider et al. | |
| 2014/0109739 A1 | 4/2014 | Schneider et al. | |
| 2016/0220423 A1 * | 8/2016 | Schneider | A61F 13/15764 |
| 2019/0008695 A1 | 1/2019 | Schneider et al. | |

FOREIGN PATENT DOCUMENTS

| | | |
|---|---|---|
| JP | 2013094618 A | 5/2013 |
| WO | 2006017718 A1 | 2/2006 |
| WO | 2010126415 A1 | 11/2010 |
| WO | 2012080851 A1 | 6/2012 |

OTHER PUBLICATIONS

All Office Actions; U.S. Appl. No. 16/129,852 filed on Sep. 13, 2018.

13179 PCT Search Report and Written Opinion for PCT/US2014/066637; dated Mar. 11, 2015, 11 pages.

* cited by examiner

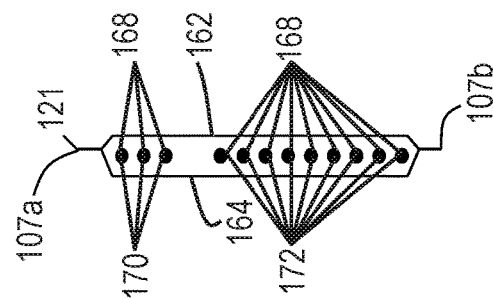
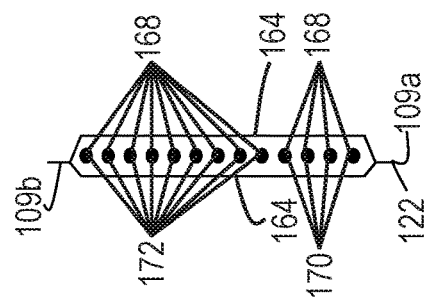
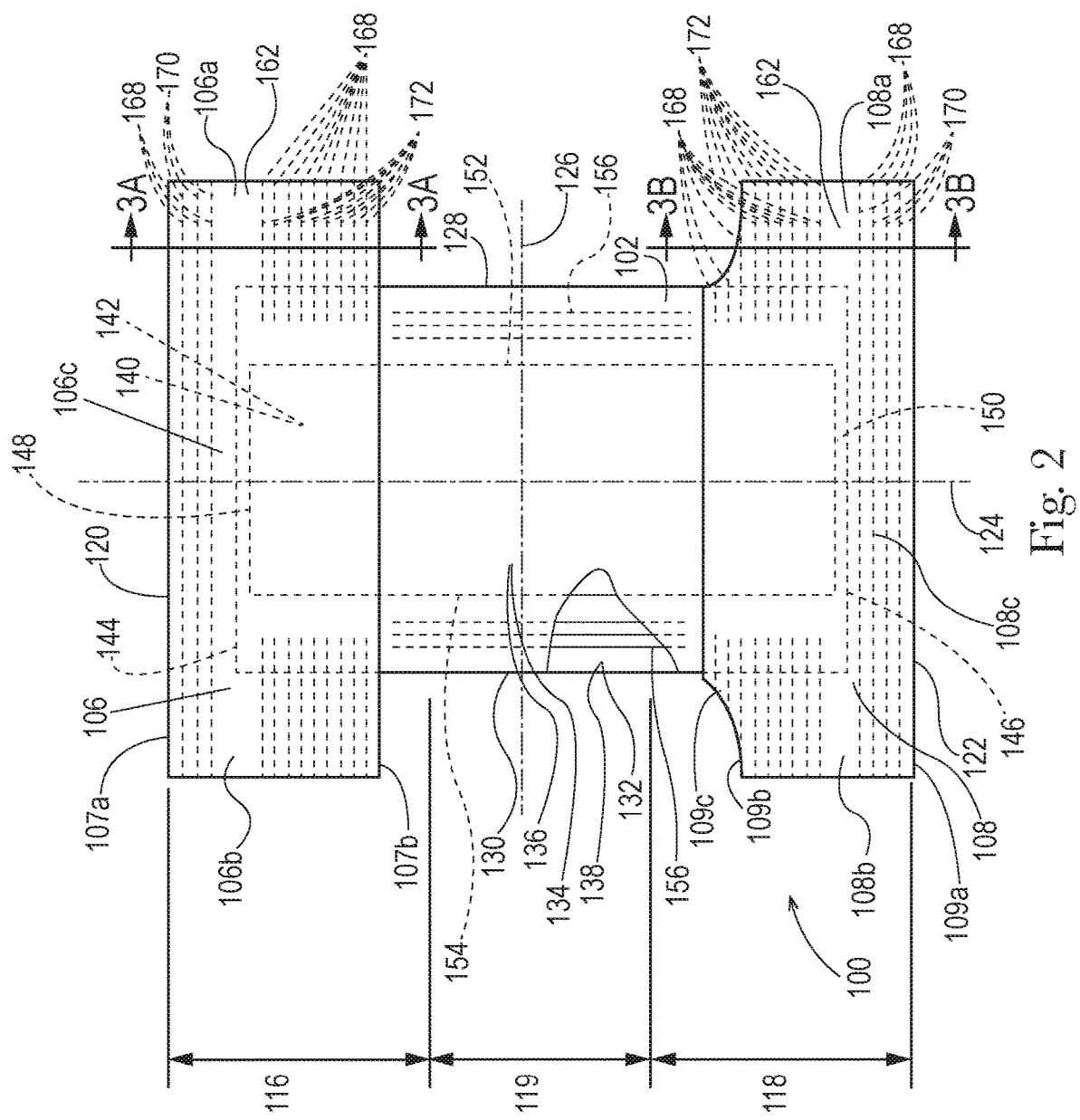

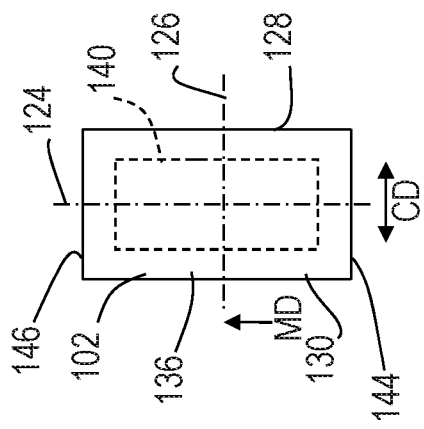
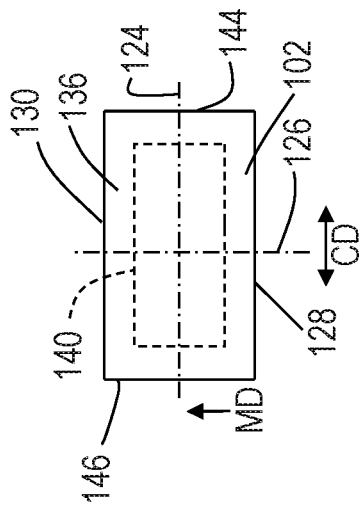
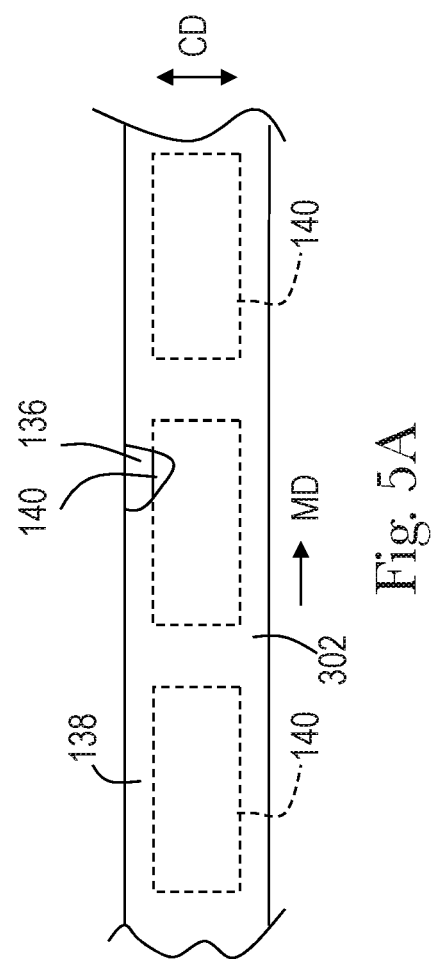
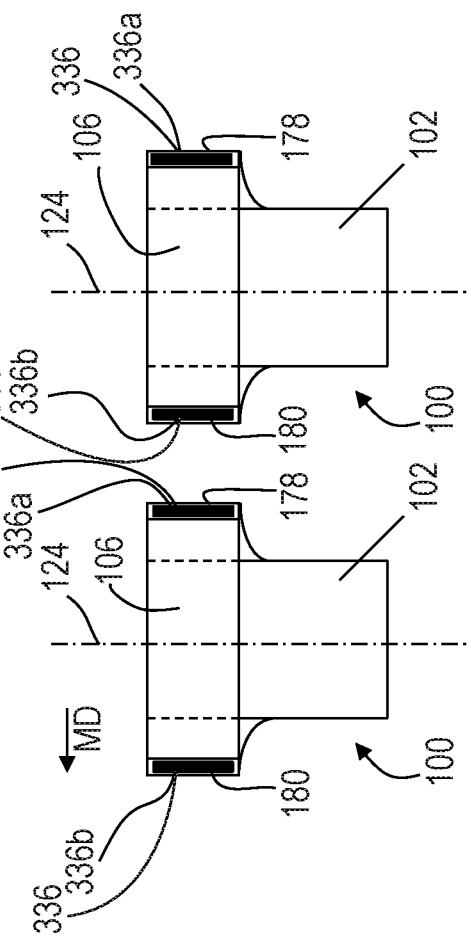

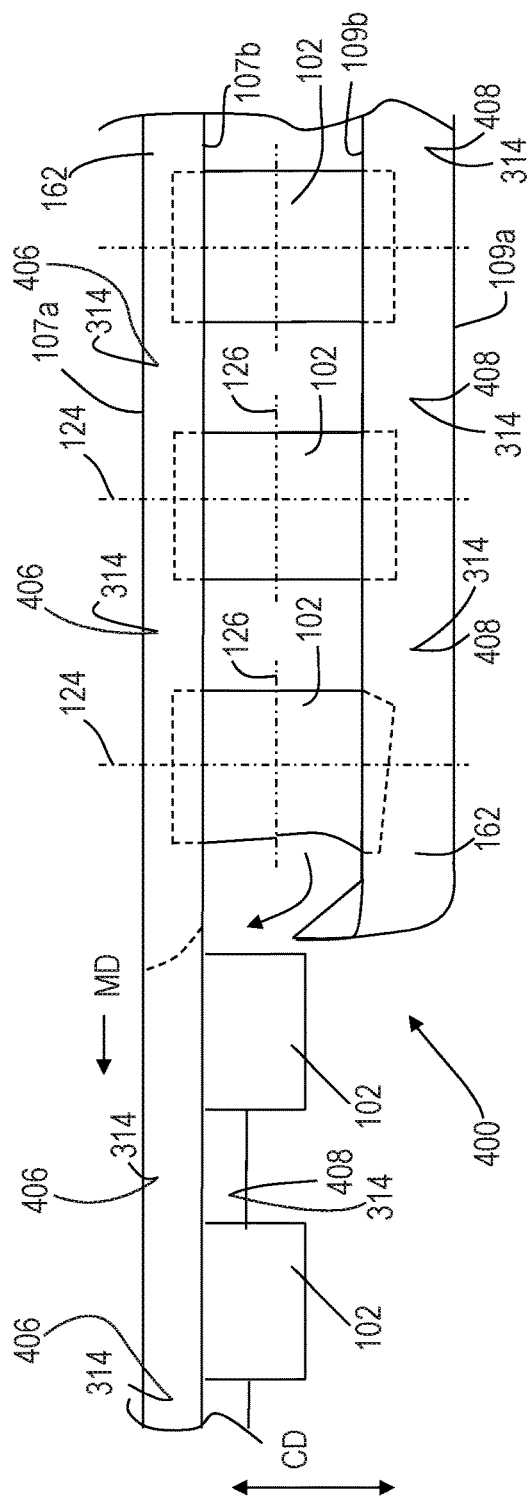
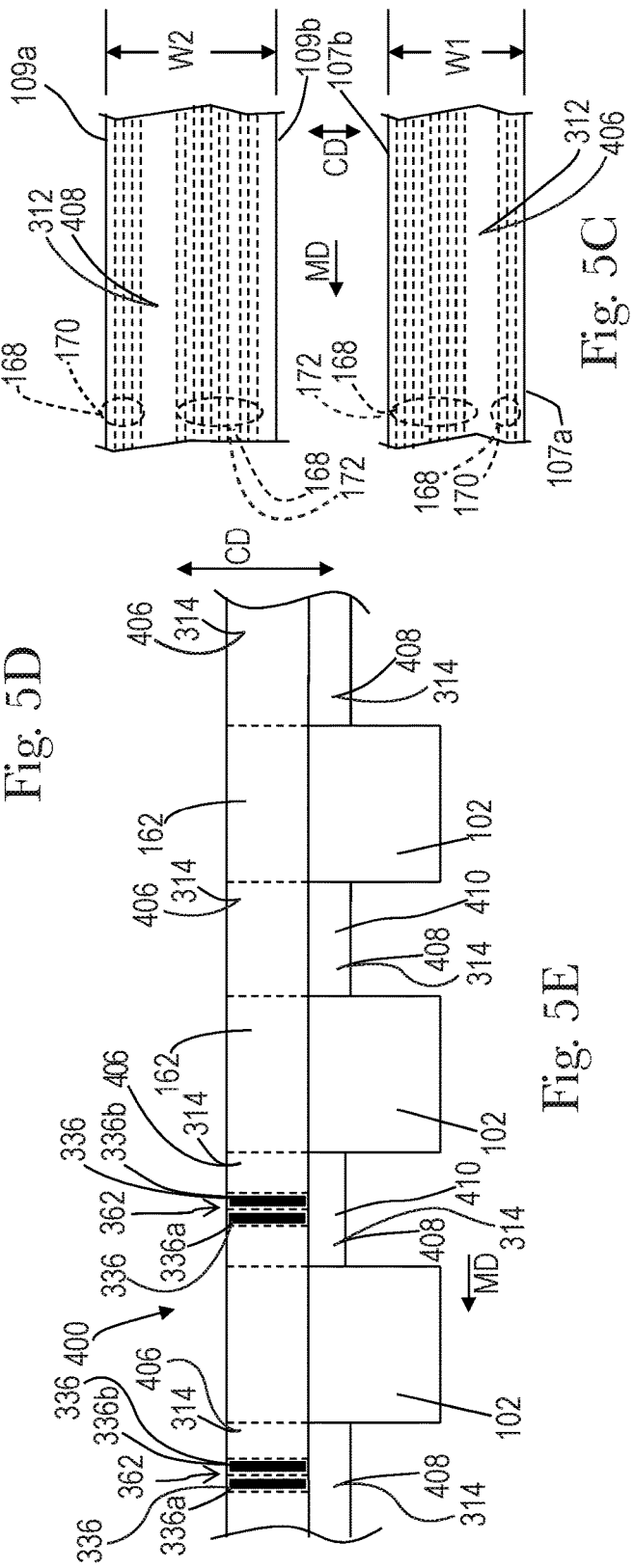
Fig. 5C
Fig. 5D
Fig. 5E

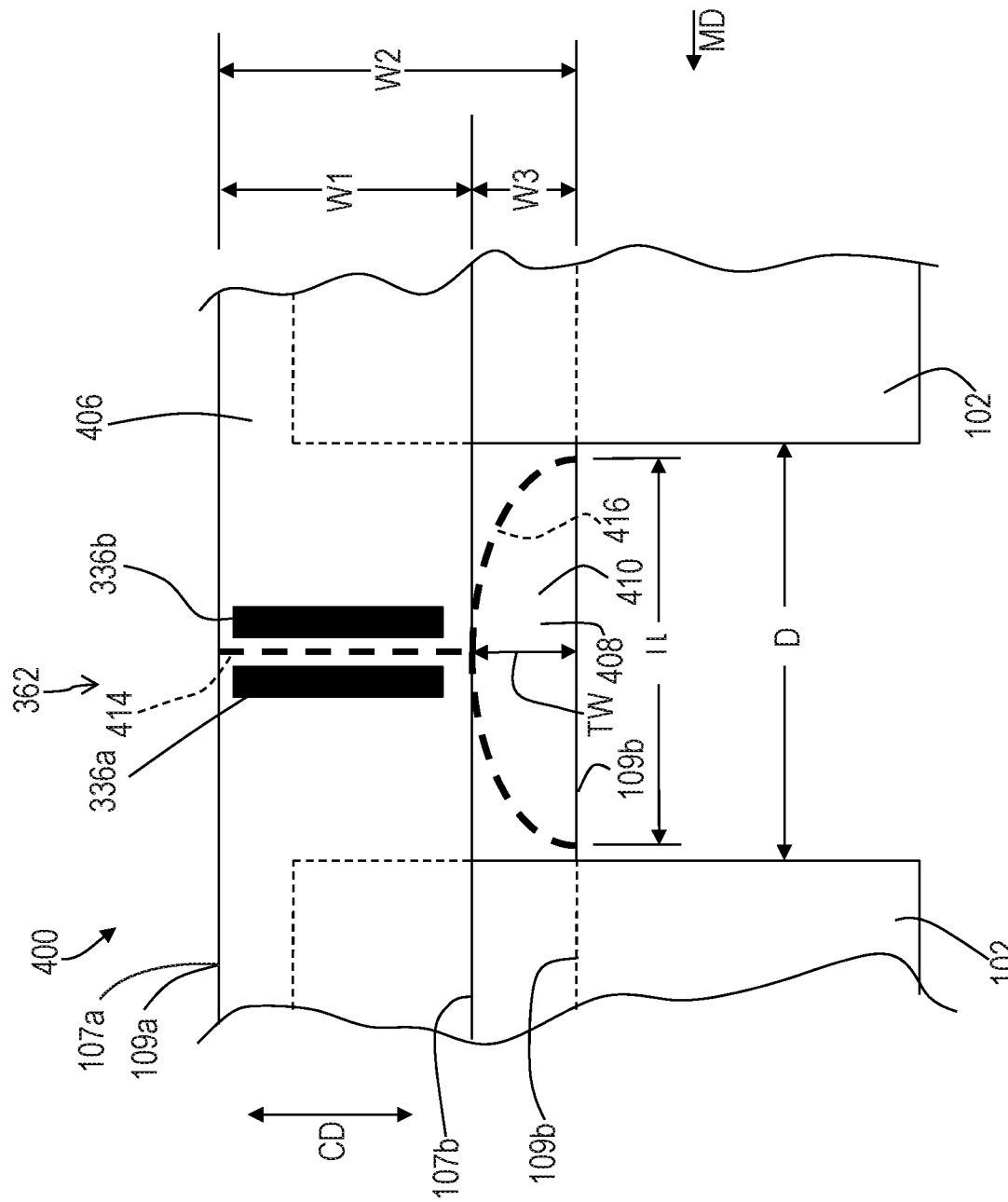
Fig. 5E1

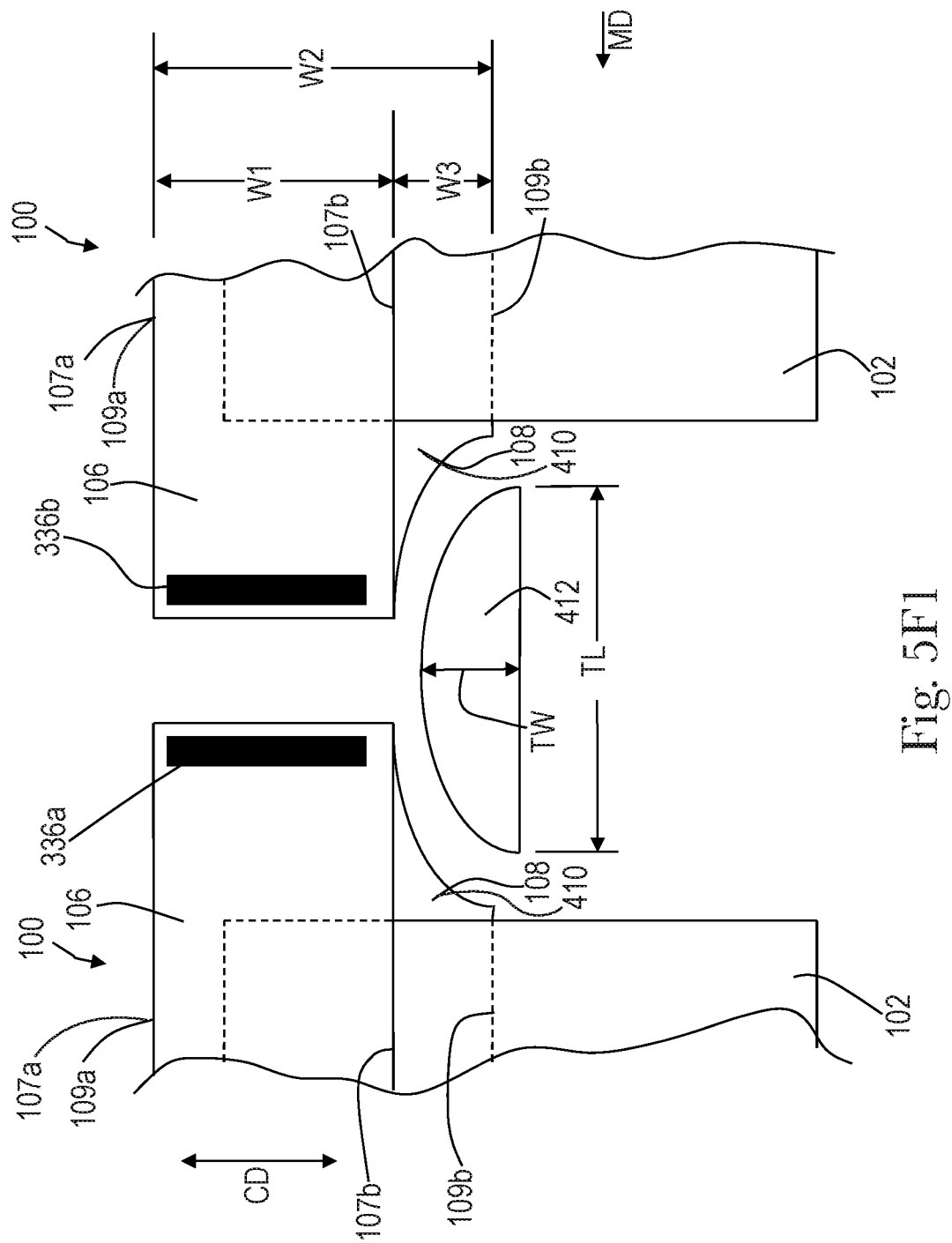
Fig. 5F1

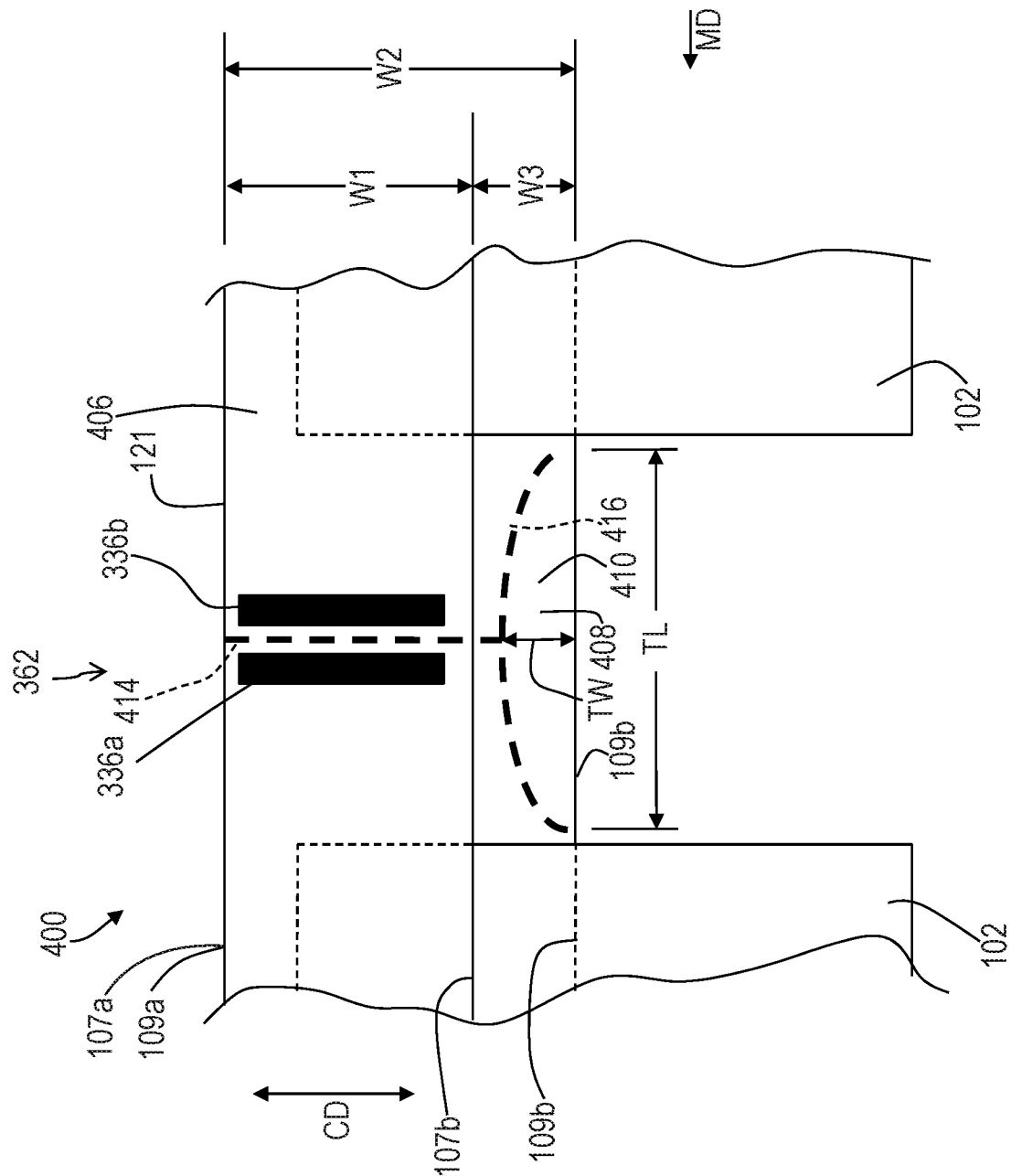
Fig. 5E2

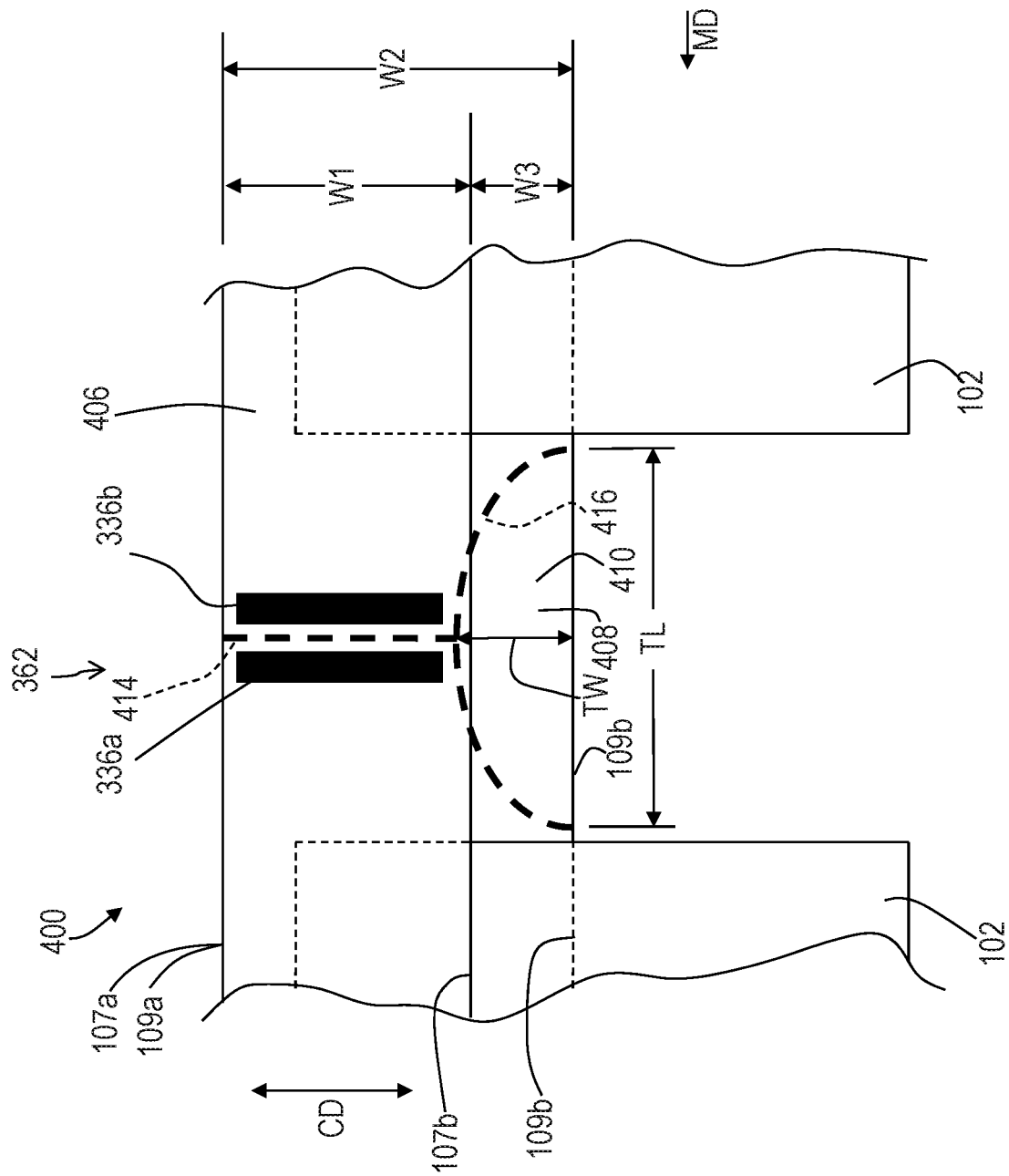
Fig. 5E3

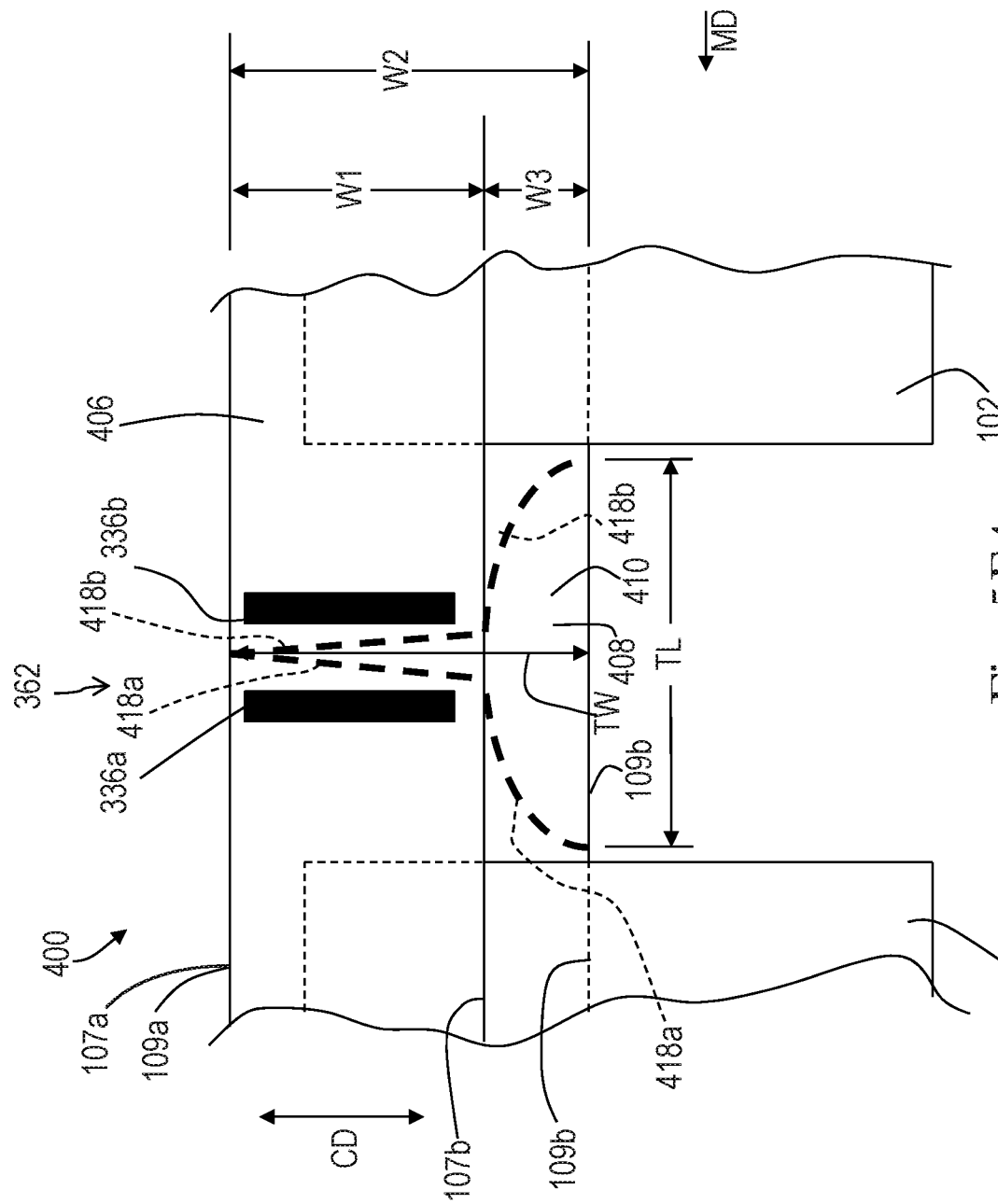
Fig. 5E4

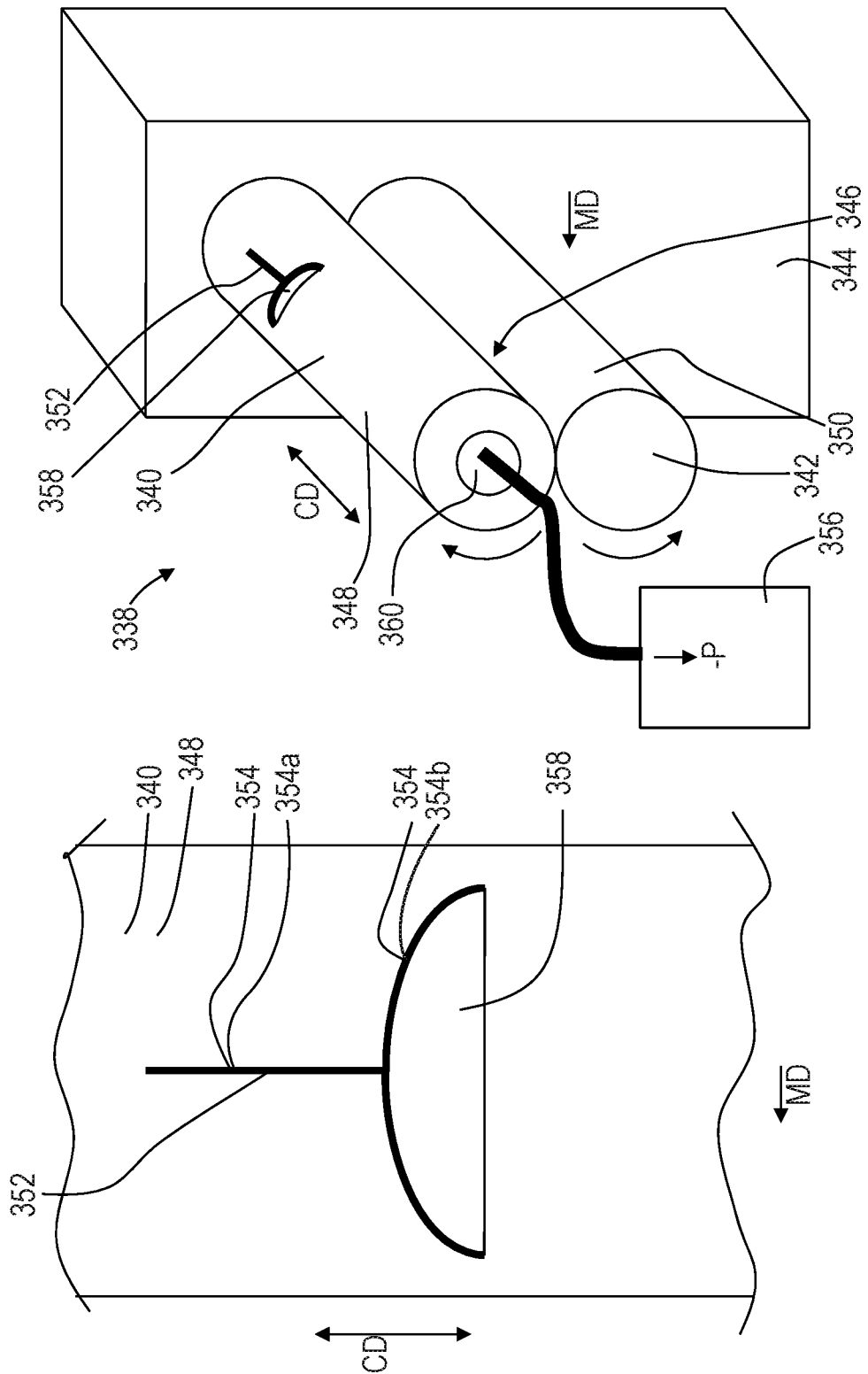

METHODS AND APPARATUSES FOR MAKING ABSORBENT ARTICLES HAVING CONTOURED BELTS

CROSS-REFERENCE TO RELATED APPLICATIONS

This application is a continuation of U.S. application Ser. No. 16/129,852, filed on Sep. 13, 2018, which is a divisional of U.S. application Ser. No. 14/559,942, filed on Dec. 4, 2014, which claims the benefit of U.S. Provisional Application No. 61/918,087, filed Dec. 19, 2013, which are all incorporated by reference herein.

FIELD OF THE INVENTION

The present disclosure relates to methods for manufacturing absorbent articles, and more particularly, to apparatuses and methods for making elastic belts for diapers.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

Some diaper pant embodiments are configured with a chassis connected with front and back elastic belts, wherein opposing end regions of the front and back belts are connected with each other at side seams. In some instances, the elasticity of the front and back belts is removed in regions where the chassis connects with the belts. Thus, in some converting configurations adapted to assemble such diaper pants, stretched elastic strands are glued between two continuous nonwoven webs to form an elastic laminate. Regions of the elastic strands may then be intermittently deactivated along the length of the elastic laminate by cutting the elastic strands. Subsequent to deactivating the elastic strands, the elastic laminate may be subjected to additional handling and converting operations.

In some instances, the diaper pants include front and back elastic belts are configured with shaped or contoured inner edges that extend along the leg openings of the diaper. Thus, in some converting configurations adapted to assemble such diaper pants, stretched elastic strands are glued between two continuous nonwoven webs to form an elastic laminate. The elastic laminate may then be cut along the machine direction in a sinusoidal or curved path to form continuous lengths of the front and back elastic belts, which are then subjected to additional handling and converting operations.

However, cutting elastic laminate in a curved path may weaken the laminate, making the laminate relatively more likely to tear, and/or may otherwise result in control and handling difficulties associated with differential stretch characteristics within the laminate. In addition, such shaping of the front and back elastic belts relatively early in the assembly process may also require relatively precise phasing and registration processes in order to ensure that the shaped areas of the belts are positioned in the desired locations of the assembled product. Consequently, it would be beneficial to provide methods and apparatuses that are configured to provide a shaped belts relatively late in the assembly process so as to minimize the handling of the shaped elastic laminates; and/or assemble the elastic laminate in such a way to maximize the aesthetic appearance of the laminate when placed in an assembled product.

SUMMARY OF THE INVENTION

The present disclosure relates to methods and apparatuses for assembling disposable pant diapers having contoured elastic belts. During the assembly process, opposing end regions of chassis are connected with the elastic belts in the form of first and second continuous elastic laminates. The chassis are then folded to place the elastic laminates into a facing relationship. The inner longitudinal edges of one or both the elastic laminates are then cut to define a contoured shape. Discrete pieces of trim material may be removed from one or both the elastic laminates, and the first and second continuous elastic laminates are cut in the cross direction to form discrete pant diapers. In some configurations, a single knife both removes the trim material and cuts the elastic laminates in cross direction. And in some configurations, a first knife removes the trim material and a second knife cuts the elastic laminates in cross direction.

In some embodiments, a method for assembling disposable pant diapers, each pant diaper including a chassis having a first end region and an opposing second end region separated from each other by a central region, and having a longitudinal axis and a lateral axis, the chassis including: a topsheet, a backsheet, and an absorbent core disposed between the topsheet and the backsheet, includes the steps of: advancing a first continuous elastic laminate along a machine direction, the first continuous elastic laminate having an outer longitudinal edge and an inner longitudinal edge defining a substantially constant width, W1, in a cross direction; advancing a second continuous elastic laminate along the machine direction, the second continuous elastic laminate having an outer longitudinal edge and an inner longitudinal edge defining a substantially constant width, W2, in the cross direction, wherein the first continuous elastic laminate is separated in the cross direction from the second continuous elastic laminate to define a gap between the inner longitudinal edge of the first continuous elastic laminate and the inner longitudinal edge of the second continuous elastic laminate; depositing a plurality of chassis spaced apart from each other along the machine direction across the gap and onto the first continuous elastic laminate and the second continuous elastic laminate, wherein the first end regions of each chassis are connected with the first continuous elastic laminate, and the second end regions of each chassis are connected with the second continuous elastic laminate; folding each chassis along the lateral axis to position the first continuous elastic laminate into a facing relationship with the second continuous elastic laminate and defining uncovered regions of the second continuous elastic laminate intermittently spaced between the chassis along the machine direction and having a width, W3, extending in the cross direction defined by a distance extending between the inner longitudinal edge of the first continuous elastic laminate and the inner longitudinal edge of the second continuous elastic laminate; removing discrete pieces of trim material from the uncovered regions of the second continuous elastic laminate; and cutting the first and second continuous elastic laminates in the cross direction to form discrete pant diapers.

In some embodiments, a method for assembling disposable pant diapers, each pant diaper including a chassis having a first end region and an opposing second end region separated from each other by a central region, and having a longitudinal axis and a lateral axis, the chassis including: a topsheet, a backsheet, and an absorbent core disposed between the topsheet and the backsheet, includes the steps of: advancing a first continuous elastic laminate along a machine direction, the first continuous elastic laminate having an outer longitudinal edge and an inner longitudinal edge; advancing a second continuous elastic laminate along the machine direction, the second continuous elastic laminate having an outer longitudinal edge and an inner longitudinal edge, wherein the first continuous elastic laminate is separated in the cross direction from the second continuous elastic laminate to define a gap between the inner longitudinal edge of the first continuous elastic laminate and the inner longitudinal edge of the second continuous elastic laminate; depositing a plurality of chassis spaced apart from each other along the machine direction across the gap and onto the first continuous elastic laminate and the second continuous elastic laminate; folding each chassis along the lateral axis to position the first continuous elastic laminate into a facing relationship with the second continuous elastic laminate and defining uncovered regions of the second continuous elastic laminate intermittently spaced between the chassis along the machine direction and having a width, W, extending in the cross direction defined by a distance extending between the inner longitudinal edge of the first continuous elastic laminate and the inner longitudinal edge of the second continuous elastic laminate; advancing the first continuous elastic laminate in the facing relationship with the second continuous elastic laminate through a nip defined between a cutting roll and an anvil roll wherein the cutting roll includes a blade having a distal edge extending in the cross direction and the machine direction; and pressing the distal edge of the blade against the first continuous elastic laminate and the second continuous elastic laminate in the nip to remove discrete pieces of trim material from the uncovered regions of the second continuous elastic laminate and to cut the first and second continuous elastic laminates in the cross direction to form discrete pant diapers.

In some embodiments, a method for assembling disposable pant diapers, each pant diaper including a chassis having a first end region and an opposing second end region separated from each other by a central region, and having a longitudinal axis and a lateral axis, the chassis including: a topsheet, a backsheet, and an absorbent core disposed between the topsheet and the backsheet, includes the steps of: advancing a first continuous elastic laminate along a machine direction, the first continuous elastic laminate having an outer longitudinal edge and an inner longitudinal edge defining a substantially constant width in a cross direction; advancing a second continuous elastic laminate along the machine direction, the second continuous elastic laminate having an outer longitudinal edge and an inner longitudinal edge defining a substantially constant width in the cross direction; depositing a plurality of chassis spaced apart from each other along the machine direction onto the first continuous elastic laminate and the second continuous elastic laminate; folding each chassis along the lateral axis to position the first continuous elastic laminate into a facing relationship with the second continuous elastic laminate to form a continuous length of absorbent articles; advancing the continuous length of absorbent articles in a first direction to a knife roll; simultaneously cutting the first and second continuous elastic laminates in the cross direction to form discrete pant diapers and cutting discrete pieces of trim material from at least one of the first continuous elastic laminate and the second continuous elastic laminate; wrapping the discrete pant diapers partially around the knife roll; advancing the discrete pant diapers in a second direction from the knife roll while holding the discrete pieces of trim material on the knife roll, wherein the second direction is different from the first direction; and removing the discrete pieces of trim material from the knife roll.

BRIEF DESCRIPTION OF THE DRAWINGS

FIG. 2 is a partially cut away plan view of the diaper pant shown in FIGS. 1A and 1B.

FIG. 3A is a cross-sectional view of the diaper pant of FIG. 2 taken along line 3A-3A.

FIG. 3B is a cross-sectional view of the diaper pant of FIG. 2 taken along line 3B-3B.

FIG. 5A is a view of a continuous length of chassis assemblies from FIG. 4 taken along line A-A.

FIG. 5B1 is a view of a discrete chassis from FIG. 4 taken along line B1-B1.

FIG. 5B2 is a view of a discrete chassis from FIG. 4 taken along line B2-B2.

FIG. 5C is a view of continuous lengths of advancing front and back side panel material from FIG. 4 taken along line C-C.

FIG. 5D is a view of multiple discrete chassis spaced from each other along the machine direction MD and connected with each other by the front and back side panel material from FIG. 4 taken along line D-D.

FIG. 5E is a view of folded multiple discrete chassis with the front and back side panel material in a facing relationship from FIG. 4 taken along line E-E.

FIG. 5E1 is a detailed view of a bonded overlapped area from FIG. 5E.

FIG. 5E2 is a detailed view of a bonded overlapped area from FIG. 5E.

FIG. 5E3 is a detailed view of a bonded overlapped area from FIG. 5E.

FIG. 5E4 is a detailed view of a bonded overlapped area from FIG. 5E.

FIG. 5F is a view of two discrete absorbent articles advancing the machine direction MD from FIG. 4 taken along line F-F.

FIG. 5F1 is a detailed view of a bonded overlapped area from FIG. 5F.

FIG. 6 is a perspective schematic view of a cutting apparatus.

FIG. 7 is a partial plan view of a knife roll.

DETAILED DESCRIPTION OF THE INVENTION

Figure 1A:
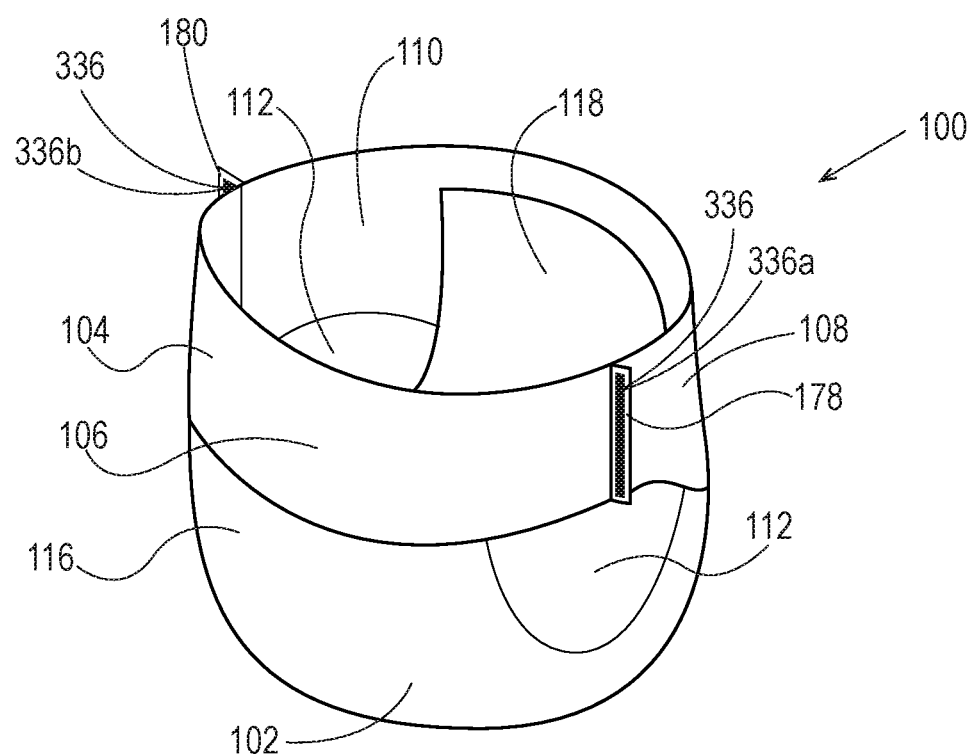
FIG. 1A is a front perspective view of a diaper pant.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

"Radial" means a direction running from the center of a drum toward a drum outer circumferential surface.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed).

The present disclosure relates to methods and apparatuses for assembling absorbent articles, and in particular, to methods and apparatuses for assembling disposable pant diapers having one or more contoured elastic belts. The diapers may each include a chassis connected with front and back elastic belts. The chassis may include a topsheet, a backsheet, and an absorbent core disposed between the topsheet and the backsheet. The chassis may also have a first end region and an opposing second end region separated from each other by a central region. During the assembly process, opposing end regions of the chassis are connected with the elastic belts in the form of first and second continuous elastic laminates. The chassis are then folded to place the elastic laminates into a facing relationship. Once the chassis are folded, the inner longitudinal edges of one or both the elastic laminates are then cut to define a contoured shape. As discussed in more detail below, discrete pieces of trim material may be removed from one or both the elastic laminates along inner longitudinal edges, and the first and second continuous elastic laminates are cut in the cross direction to form discrete pant diapers. In some configurations, a single knife both removes the trim material and cuts the elastic laminates in cross direction. While in other configurations, a first knife removes the trim material and a second knife cuts the elastic laminates in cross direction. In such process configurations, the required handling of the shaped elastic laminates is minimized, because contouring of the elastic belts is performed near the end of the diaper assembly process.

As previously mentioned, the processes and apparatuses discussed herein may be used in the manufacture of different types of absorbent articles. To help provide additional context to the subsequent discussion of the process embodiments, the following provides a general description of absorbent articles in the form of diaper pants that include belt substrates that may be cut in accordance with the methods and apparatuses disclosed herein.

Figure 1B:
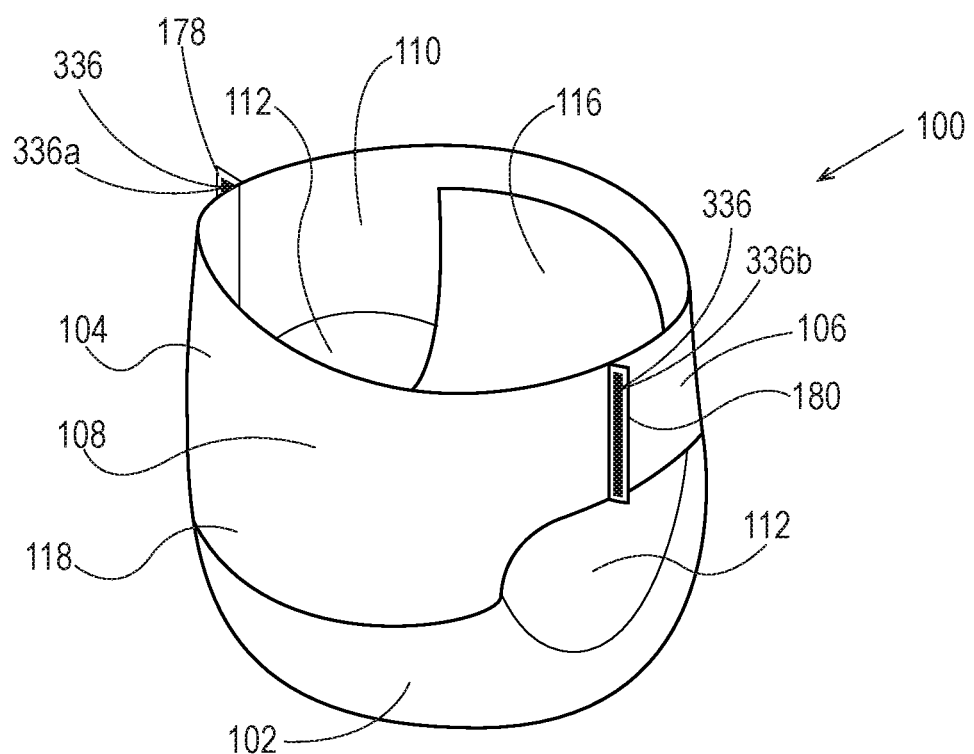
FIG. 1B is a rear perspective view of a diaper pant.

FIGS. 1A, 1B, and 2 show an example of a diaper pant 100 that may be assembled and folded in accordance with the apparatuses and methods disclosed herein. In particular, FIGS. 1A and 1B show perspective views of a diaper pant 100 in a pre-fastened configuration, and FIG. 2 shows a plan view of the diaper pant 100 with the portion of the diaper that faces away from a wearer oriented toward the viewer. The diaper pant 100 shown in FIGS. 1A, 1B, and 2A includes a chassis 102 and a ring-like elastic belt 104. As discussed below in more detail, a first elastic belt 106 and a second elastic belt 108 are bonded together to form the ring-like elastic belt 104. Although only the second elastic belt 108 is shown with a contoured or shaped edge, it is to be appreciated that either or both the first elastic belt 106 and second elastic belt 108 may include shaped edges made in accordance with the apparatuses and processes herein.

With continued reference to FIG. 2, the chassis 102 includes a first waist region 116, a second waist region 118, and a crotch region 120 disposed intermediate the first and second waist regions. The first waist region 116 may be configured as a front waist region, and the second waist region 118 may be configured as back waist region. In some embodiments, the length of each of the front waist region, back waist region, and crotch region may be ⅓ of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the diaper 100 and chassis 102 of FIG. 2 are shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1A, 1B, and 2, the diaper pant 100 may include an inner, body facing surface 132, and an outer, garment facing surface 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100 may also include other features, such as leg elastics and/or leg cuffs to enhance the fit around the legs of the wearer.

As shown in FIG. 2, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 2, the laterally extending end edges 144 and 146 are located longitudinally inward from the laterally extending front waist edge 121 in the front waist region 116 and the laterally extending back waist edge 122 in the back waist region 118. When the diaper pant 100 is worn on the lower torso of a wearer, the front waist edge 121 and the back waist edge 122 of the chassis 102 may encircle a portion of the waist of the wearer. At the same time, the chassis side edges 128 and 130 may encircle at least a portion of the legs of the wearer. And the crotch region 120 may be generally positioned between the legs of the wearer with the absorbent core 142 extending from the front waist region 116 through the crotch region 120 to the back waist region 118.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, the user of the diaper 100, including a chassis 102 having a particular size before extension, to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper pant 100 may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 140 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper pant 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper pant 100 may also include an absorbent assembly 140 that is joined to the chassis 102. As shown in FIG. 2, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

As previously mentioned, the diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; and U.S. Patent Publication No. 2009/0312730A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIGS. 1A and 1B.

As previously mentioned, the ring-like elastic belt 104 is defined by a first elastic belt 106 connected with a second elastic belt 108. As shown in FIG. 2, the first elastic belt 106 defines first and second opposing end regions 106a, 106b and a central region 106c, and the second elastic 108 belt defines first and second opposing end regions 108a, 108b and a central region 108c. The central region 106c of the first elastic belt is connected with the first waist region 116 of the chassis 102, and the central region 108c of the second elastic belt 108 is connected with the second waist region 116 of the chassis 102. As shown in FIGS. 1A and 1B, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 107b may also define the front waist edge 120 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, films, or panels extending along the lengths of the elastic belts. As shown in FIGS. 2, 3A, and 3B, the belt elastic material may include a plurality of elastic strands 168 which may be referred to herein as outer, waist elastics 170 and inner, waist elastics 172. As shown in FIG. 2, the elastic strands 168 continuously extend laterally between the first and second opposing end regions 106a, 106b of the first elastic belt 106 and between the first and second opposing end regions 108a, 108b of the second elastic belt 108. In some embodiments, some elastic strands 168 may be configured with discontinuities in areas, such as for example, where the first and second elastic belts 106, 108 overlap the absorbent assembly 140. In some embodiments, the elastic strands 168 may be disposed at a constant interval in the longitudinal direction. In other embodiments, the elastic strands 168 may be disposed at different intervals in the longitudinal direction. The belt elastic material in a stretched condition may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2.

In some configurations, the first elastic belt 106 and/or second elastic belt 108 may define curved contours. For example, as shown in FIG. 2, the inner lateral edge 109b of the second elastic belt 108 may include non-linear or curved portions 109c in the first and second opposing end regions 108a, 108b. Such curved contours may help define desired shapes to leg opening 112, such as for example, relatively rounded leg openings. Although the inner lateral edge 107b of the first elastic belt is depicted as being a straight line, it is to be appreciated that the inner lateral edge 107b may also include curved portions in the first and second opposing end regions 106a, 106b. In addition to having curved contours, the elastic belts 106, 108 may include elastic strands 168, 172 that extend along non-linear or curved paths that may correspond with the curved contours of the inner lateral edges 107b, 109b. As discussed below, such non-linear or curved contours may be applied to the inner lateral edges 107b, 109b with the methods and apparatuses herein.

Figure 4:
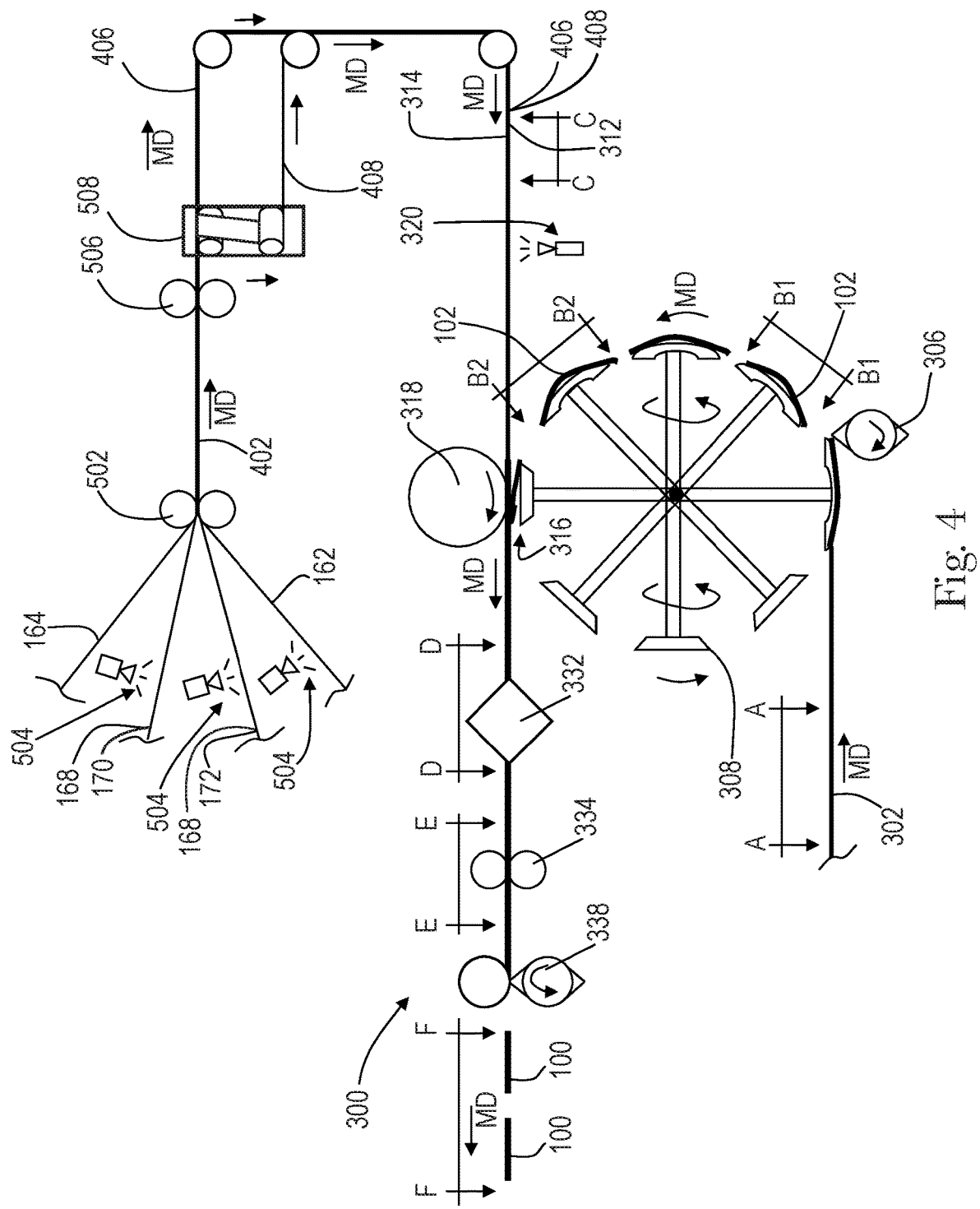
FIG. 4 is a schematic side view of a converting apparatus adapted to manufacture pre-fastened, pant diapers.

As previously mentioned, the apparatuses and methods according to the present disclosure may be utilized to assemble various components of pre-fastened, refastenable pant diapers 100. For example, FIG. 4 shows a schematic view of a converting apparatus 300 adapted to manufacture pant diapers 100. The method of operation of the converting apparatus 300 may be described with reference to the various components of pant diapers 100 described above and shown in FIGS. 1A, 1B, and 2. Although the following methods are provided in the context of the diaper 100 shown in FIGS. 1A, 1B, and 2, it is to be appreciated that various embodiments of diaper pants can be manufactured according to the methods disclosed herein, such as for example, the absorbent articles disclosed in U.S. Pat. No. 7,569,039; U.S. Patent Publication Nos. 2005/0107764A1, 2012/0061016A1, and 2012/0061015A1, which are all hereby incorporated by reference herein.

As described in more detail below, the converting apparatus 300 shown in FIG. 4 operates to advance discrete chassis 102 along a machine direction MD such that the lateral axis of each chassis 102 is parallel with the machine direction, and wherein the chassis 102 are spaced apart from each other along the machine direction. Opposing waist regions 116, 118 of the spaced apart chassis 102 are then connected with continuous lengths of advancing first and second elastic belt laminates 406, 408. The chassis 102 are then folded along the lateral axis to bring the first and second elastic belt laminates 406, 408 into a facing relationship, and the first and second elastic belt laminates are bonded together with bonds 336. As discussed in more detail below, the first and second elastic belt laminates may be bonded together with adjacent bonds 336a, 336b intermittently spaced along the machine direction. Each bond 336a, 336b may be a discrete bond site extending contiguously in the cross direction across a width of the first and second elastic belt laminates and/or may include a plurality of relatively small, discrete bond sites arranged in the cross direction. Next, discrete pieces of trim material are removed regions of the first and/or second elastic belt laminates 406, 408 extending between adjacent folded chassis. The first and second continuous elastic laminates 406, 408 are cut in the cross direction between adjacent bonds 336a, 336b to create discrete pant diapers 100, such as shown in FIGS. 1A and 1B.

As shown in FIG. 4, a first continuous substrate layer in the form of a continuous length of outer layer belt material 162; a second continuous substrate layer in the form of a continuous length of inner layer belt material 164; and elastics 168 are combined to form a continuous elastic laminate in the form of a belt material 402. More particularly, continuous lengths of outer layer belt material 162, inner layer belt material 164, outer elastic strands 170 and inner elastic strands 172 are advanced in a machine direction MD and combined at nip rolls 502 to form a continuous length of belt material 402. Before entering the nip rolls 502, the outer elastic strands 170 and inner elastic strands 172 are stretched in the machine direction MD. In addition, adhesive 504 may applied to the elastic strands 170, 172 as well as either or both of the continuous lengths of outer layer belt material 162 and inner layer belt material 164 before entering nip rolls 502. Further, adhesive 504 may be applied intermittently along the lengths of the inner elastic strands 172 and/or intermittently along the length of either or both of the continuous lengths of outer layer belt material 162 and inner layer belt material 164 before entering nip rolls 502. As such, the inner elastic strands 172 may be intermittently bonded to either or both of the continuous lengths of outer layer belt material 162 and inner layer belt material 164 along the machine direction MD. Thus, the belt material 402 may include non-bonded regions intermittently spaced between bonded regions along the machine direction MD, wherein the inner elastic strands 172 are not bonded to either the outer layer belt material 162 or inner layer belt material 164 in the non-bonded regions. And the inner elastic strands 172 are bonded to the outer layer belt material 162 and/or inner layer belt material 164 in the bonded regions. Although FIG. 4 shows an embodiment wherein the belt material 402 is formed by combining continuous lengths of outer layer belt material 162 and inner layer belt material 164 with elastic strands 168, it is to be appreciated the belt material 402 can be formed in various ways, such as disclosed in U.S. Pat. No. 8,440,043 and U.S. Patent Publication Nos. US2013/0255861A1; US2013/0255862A1; US2013/0255863A1; US2013/0255864A1; and US2013/0255865A1.

Referring back to FIG. 4, from the nip rolls 502 the continuous length of belt material 402 advances in the machine direction MD to a cutter 506 that cuts the belt material 402 into two continuous belt substrates, referred to as a first belt substrate 406 and a second belt substrate 408. The cutter 506 may be configured in various ways. For example, in some embodiments the cutter 506 may be a slitter or a die cutter that separates the belt material into two continuous belt substrates with either a straight line cut and/or a curved line cut. The cutter 506 may also be configured as a perforator that perforates the belt material with a line of weakness and wherein the belt material is separated along the line of weakness in a later step. From the cutter 506, the first and second belt substrates 406, 408 advance through a diverter 508 that separates the first and second belt substrates from each other in the cross direction CD, such as shown in FIG. 5B. The elastic strands 170, 172, and thus, the continuous length of first and second belt substrates 406, 408 are maintained in a stretched condition while advancing along the machine direction MD. It is to be appreciated that the diverter 508 may be configured in various ways. For example, in some embodiments, the diverter 508 may include turn bars angled at 45 degrees or some other angle with respect to the machine direction. In some embodiments, the diverter may include cambered rollers. Other embodiments may include diverters in the form of a pivot table, such as, for example, the FIFE-500 Web Guiding System, by Maxcess-FIFE Corporation. The diverter may also include instrumentation and web edge control features that allow for precise active control of the substrate positions.

As shown in FIG. 5C, the first belt substrate 406 includes an outer longitudinal edge 107a and an inner longitudinal edge 107b defining a substantially constant width, W1, in a cross direction. And the second belt substrate 408 includes an outer longitudinal edge 109a and an inner longitudinal edge 109b defining a substantially constant width, W2, in a cross direction, wherein W2 is greater than W1. It is to be appreciated that in some configurations, W1 may be equal to or greater than W2. As previously mentioned, the first belt substrate 406 is separated in the cross direction from the second belt substrate 408 to define a gap between the inner longitudinal edge 107b of the first belt substrate 406 and the inner longitudinal edge 109b of the second belt substrate 408. As discussed in more detail below, the first and second belt substrates 406, 408 advance from the diverter 508 to a nip 316 between the carrier apparatus 308 and a carrier apparatus 318 to be combined with discrete chassis 102.

As shown in FIGS. 4 and 5A, a continuous length of chassis assemblies 302 are advanced in a machine direction MD to a carrier apparatus 308 and cut into discrete chassis 102 with knife roll 306. The continuous length of chassis assemblies may include absorbent assemblies 140 sandwiched between topsheet material 138 and backsheet material 136, leg elastics, barrier leg cuffs and the like. As shown in FIG. 5A, portion of the chassis assembly is cut-away to show a portion of the topsheet material 138 and an absorbent assembly 140.

After the discrete absorbent chassis 102 are cut by the knife roll 306, the carrier apparatus 308 rotates and advances the discrete chassis 102 in the machine direction MD in the orientation shown in FIG. 5B1, wherein the longitudinal axis 124 of the chassis 102 is generally parallel with the machine direction MD. While the chassis 102 shown in FIG. 5B1 is shown with the second laterally extending end edge 146 as a leading edge and the first laterally extending end edge 144 as the trailing edge, it is to be appreciated that in other embodiments, the chassis 102 may be advanced in other orientations. For example, the chassis may be oriented such that the second laterally extending end edge 146 is a trailing edge and the first laterally extending end edge 144 is a leading edge. The carrier apparatus 308 also rotates while at the same time changing the orientation of the advancing chassis 102. The carrier apparatus 308 may also change the speed at which the chassis 102 advances in the machine direction MD. It is to be appreciated that various forms of carrier apparatuses may be used with the methods herein, such as for example, the carrier apparatuses disclosed in U.S. Pat. No. 7,587,966. FIG. 5B2 shows the orientation of the chassis 102 on the carrier apparatus 308 while advancing in the machine direction. More particularly, FIG. 5B2 shows the chassis 102 with the lateral axis 126 of the chassis 102 generally parallel with the machine direction MD, and wherein the second longitudinal side edge 130 is the leading edge and the first longitudinal side edge 128 is the trailing edge.

As discussed below with reference to FIGS. 4, 5C, 5D, 5E, and 5F, the chassis 102 are transferred from the carrier apparatus 308 and combined with advancing, continuous lengths of belt laminates 406, 408, which are subsequently cut to form first and second elastic belts 106, 108 on diapers 100.

With reference to FIGS. 4 and 5C, the chassis 102 are transferred from the carrier apparatus 308 to a nip 316 between the carrier apparatus 308 and a carrier apparatus 318 where the chassis 102 is combined with continuous lengths of advancing front belt 406 and back belt 408 substrate material. The front belt laminate material 406 and the back belt laminate material 408 each define a wearer facing surface 312 and an opposing garment facing surface 314. The wearer facing surface 312 of the first belt laminate 406 may be combined with the garment facing surface 134 of the chassis 102 along the first waist region 116, and the wearer facing surface 312 of the second belt laminate 408 may be combined with the garment facing surface 134 of the chassis 102 along the second waist region 118. As shown in FIG. 4, adhesive 320 may be intermittently applied to the wearer facing surface 312 of the first and second belt laminates 406, 408 before combining with the discrete chassis 102 at the nip 316 between roll 318 and the carrier apparatus 308.

With reference to FIGS. 4 and 5D, a continuous length of absorbent articles 400 are defined by multiple discrete chassis 102 spaced from each other along the machine direction MD and connected with each other by the second belt laminate 408 and the first belt laminate 406. As shown in FIG. 4, the continuous length of absorbent articles 400 advances from the nip 316 to a folding apparatus 332. At the folding apparatus 332, each chassis 102 is folded in the cross direction CD along a lateral axis 126 to place the first waist region 116, and specifically, the inner, body facing surface 132 into a facing, surface to surface orientation with the inner, body surface 132 of the second waist region 118. The folding of the chassis also positions the wearer facing surface 312 of the second belt laminate 408 extending between each chassis 102 in a facing relationship with the wearer facing surface 312 of the first belt laminate 406 extending between each chassis 102. As shown in FIGS. 4, 5D, and 5E, the folded discrete chassis 102 connected with the first and second belt laminates 406, 408 are advanced from the folding apparatus 332 to a bonder apparatus 334. The bonder apparatus 334 operates to bond an overlap area 362, thus creating discrete bonds 336a, 336b. The overlap area 362 includes a portion of the second belt laminate 408 extending between each chassis 102 and a portion of the first belt laminate 406 extending between each chassis 102.

As previously mentioned, the first belt laminate 406 may define a first width, W1, in the cross direction CD and the second belt laminate may define a second width, W2, in the cross direction CD, wherein W2 is greater than W1. Thus, as shown in FIGS. 5E and 5E1, folding each chassis 102 and positioning the first belt laminate 406 into a facing relationship with the second belt laminate 408 may define uncovered regions 410 of the second belt laminate 408 intermittently spaced between the chassis 102 along the machine direction MD. The uncovered regions 410 may have a width, W3, extending in the cross direction defined by a distance extending between the inner longitudinal edge 107b of the first belt laminate 406 and the inner longitudinal edge 109b of the second belt laminate 408. It is to be appreciated that folding each chassis 102 and positioning the first belt laminate 406 into a facing relationship with the second belt laminate 408 may also include aligning the outer longitudinal edge 107a of the first belt laminate 406 with the outer longitudinal edge 109a of the second belt laminate 408.

As shown in FIGS. 4 and 5F, the continuous length of absorbent articles 400 are advanced from the bonder 334 to a cutting apparatus 338 where the first belt laminate 406 and the second belt laminate 408 are cut along the cross direction CD between adjacent bonds 336a, 336b to create discrete absorbent articles 100. As such, bond 336a may correspond with and form a first side seam 178 on an absorbent article 100, and the bond 336b may correspond with and form a second side seam 180 on a subsequently advancing absorbent article.

In addition to cutting the first belt laminate 406 and the second belt laminate 408 along the cross direction CD between adjacent bonds 336a, 336b, the cutting apparatus 338 may also be configured to remove discrete pieces of trim material 412 from the uncovered regions 410 of the second belt laminate 408, such as shown in FIGS. 5E1 and 5F1. As shown in FIG. 5E1, the cutting apparatus 338 may be configured to cut the first and second belt laminates 406, 408 along a first cut line 414 and a second cut line 416. The first cut line 414 may extend in a cross direction CD to sever the first and second belt laminates 406, 408. And the second cut line may extend in the machine direction and cross direction to sever the pieces of trim material 412 from the first belt laminate 406 and/or the second belt laminate 408. As such, the cutting apparatus 338 may be configured to cut discrete absorbent articles 100 from the continuous length of absorbent articles 400 while at the same time forming contoured and/or shaped front and/or back elastic belts 106, 108 on the absorbent articles 100. As discussed below, the processes and apparatuses herein may be configured to produce absorbent articles 100 having a front elastic belt 106 with a substantially constant width and a back elastic belt 108 having a variable width defined by a contoured or shaped edge 109b.

It is to be appreciated that that the first and second cut lines may be configured in various ways. For example, as shown in FIGS. 5E1 and 5F1, the first cut line 414 may extend in a straight line in the cross direction CD to intersect with the second cut line 416. The second cut line may extend in a curved path to define a length TL in the machine direction MD. As shown in FIG. 5E1, the adjacent chassis 102 may be separated from each other in the machine direction MD by a distance D, and as such, the second cut line 416 may have a length TL that is equal to or less then the distance D such that the chassis 102 are not cut while removing the trim material 412. However, in some embodiments, the length TL may be greater than the distance D. The second cut line 416 may also intersect with and extend in the cross direction CD from the inner longitudinal edge 107b and/or inner longitudinal edge 109b of the first and/or second belt laminates 406, 408. For example, as shown in FIG. 5E1, the second cut line 416 extends in the cross direction CD from the inner longitudinal edge 109b of the second belt laminate 408 a distance TW to intersect with the first cut line 414. Thus, as shown in FIG. 5F1, the piece of trim material 412 may have a corresponding length TL and width TW.

It is to be appreciated that the first cut line 414 may extend along a straight and/or curved path along the cross direction CD. In addition, the first cut line 414 may be perpendicular with respect to the outer longitudinal edge 107a and/or outer longitudinal edge 109a of the first and/or second belt laminates 406, 408. In some configurations, the first cut line 414 may be define an angle that is less than 90° with respect to the outer longitudinal edge 107a and/or outer longitudinal edge 109a. In addition, it is to be appreciated that the second cut line 416 may extend along a path define by straight and/or curved portions.

With continued reference to FIGS. 5E1 and 5F1, the cutting apparatus 338 may be configured to remove trim material 412 from only the uncovered regions 410 of the second belt laminate 408 without removing material from the first belt laminate 406. For example, the first cut line 414 may extend from the outer longitudinal edges 107a, 109a of the first and second belt laminates 406, 408 to the inner longitudinal edge 107b of the first belt laminate 406. And the second cut line 416 may extend a distance TW in the cross direction from the inner longitudinal edge 109b of the second belt laminate 408 to inner longitudinal edge 107b of the first belt laminate 406 without crossing the inner longitudinal edge 107b. As such, in some configurations, the width TW of the trim material 412 may be the equal to or substantially equal to the width W3 of the uncovered region 410. In some configurations, the second cut line 416 may extend a distance TW in the cross direction from the inner longitudinal edge 109b of the second belt laminate 408 that is less than the width W3 of the uncovered region 410, such as shown in FIG. 5E2. And in some configurations, the second cut line 416 may extend a distance TW in the cross direction from the inner longitudinal edge 109b of the second belt laminate 408 that is greater than the width W3 of the uncovered region 410, such as shown in FIG. 5E3. As such, the second cut line 416 may cross the inner longitudinal edge 107b of the first belt laminate 406, and thus, the trim material 412 may include a portion of the first belt laminate 406 as well as the second belt laminate 408.

With reference to FIG. 5E4, the cutting apparatus 338 may also be configured to such to sever the first and second belt laminates 406, 408 with a pair of cut lines 418a, 418b extending in the cross direction CD and diverging from each other the machine direction MD. As such, the pair of cut lines 418a, 418b may define a piece of trim material 412 the extends in the machine direction MD between adjacent bonds 336a, 336b as well as extending in the cross direction CD from the outer longitudinal edges 107a, 109a of the first and second belt laminates 406, 408 to the inner longitudinal edges 107b, 109b.

It is to be appreciated that the cutting apparatus 338 may be configured in various ways. For example, as shown in FIGS. 6 and 7, the cutting apparatus 338 may include a cutting roll 340 and an anvil roll 342 rotatably connected with a frame 344. Various types of cutting roll, anvil roll, and frame arrangements may be utilized, such as disclosed for example in U.S. Pat. No. 7,971,525. More particularly, the cutting roll 340 and the anvil roll 342 may be adapted to rotate in opposing directions. And the cutting roll 340 may be positioned adjacent the anvil roll 342 to define a nip 346 therebetween. As shown in FIG. 6, the cutting roll 340 may include an outer circumferential surface 348, and the anvil roll 342 may include an outer circumferential surface 350. The cutting roll 340 may also include one or more blades 352. As shown in FIG. 7, the blade 352 may include a distal edge 354 having a first portion 354a that extends in the cross direction CD and a second portion 354b that extends in the machine direction MD and cross direction CD. As such, the first portion 354a of the distal edge 354 may correspond with the first cut line 414 discussed above, and the second portion 354b of the distal edge 354 may correspond with the second cut line 416 discussed above. Thus, in operation, a continuous length of absorbent articles 400 may advance in the machine direction MD through the nip 346 between the rotating cutting roll 340 and anvil roll 342. And the distal edge 354 of the blade 352 presses the first and second belt substrates 406 and 408 against the outer circumferential surface 350 of the anvil roll 350 to separate or cut discrete absorbent articles 100 from the continuous length of absorbent articles 400, while at the same time removing discrete pieces of trim material 412 to form contoured and/or shaped front and/or back elastic belts 106, 108 on the absorbent articles 100.

The processes and apparatuses herein may also be configured in various ways to remove the pieces of trim material 412 from the cutting apparatus 338. In some configurations, the cutting roll and/or anvil roll may be configured as a cantilevered unit where the open cutting roll end of the cantilevered unit is used for the trim removal. For example, as shown in FIG. 6, a vacuum system 356 may be fluidly connected with the cutting roll 340 to pull pieces of trim material 412 from the cutting roll 340. More particularly, as shown in FIGS. 6 and 7, the cutting roll 340 may include an aperture 358 in the outer circumferential surface 348 adjacent the blade 352. In turn, the aperture may be fluidly connected to a channel 360 extending through the interior of the cutting roll 340, wherein the channel 360 is fluidly connected with the vacuum system 356. During operation, the vacuum system 356 may pull the cut pieces of trim material 412 through the aperture 358 in the cutting roll 340 and the through the channel 360 from inside in the cutting roll 340. As shown in FIG. 7, the aperture 358 may have perimeter that defines a shape that is substantially the same as the pieces of trim material 412. In addition, because the belt laminates being cut may include stretched elastic strands, the trim material may contract in the in the width and length directions while being cut. As such, the contraction in size of the trim material may help the trim material pass through aperture relatively easier. Also, upon separation of the elastic strands will help promote the separation of cut or partially cut nonwoven fibers.

It is to be appreciated that the cutting roll 340 may be configured in various ways. For example, in some embodiments, the cutting roll 340 may be configured so as to cut one product contour per revolution. Such a configuration may allow the vacuum system to remain turned on during the entire cutting cycle, whereas cutting roll configured to cut more than one product per revolution may require an on/off cycle for the vacuum system.

In some embodiments, the cutting roll 340 may include bearer rings and the distal edge of the blade is smaller in diameter than the diameter of the bearer ring, which reduce the tendency to vibrate due to the imbalance of cutting force during the crosscut. In some embodiments, the diameter of the distal cutting edge may be about 1 to 10 micron smaller in diameter than the bearer ring. In some embodiments, the cutting roll may be configured such that the diameter defined by the distal edge of the blade is equal to or greater than the diameter of the bearer ring.

Figure 8:
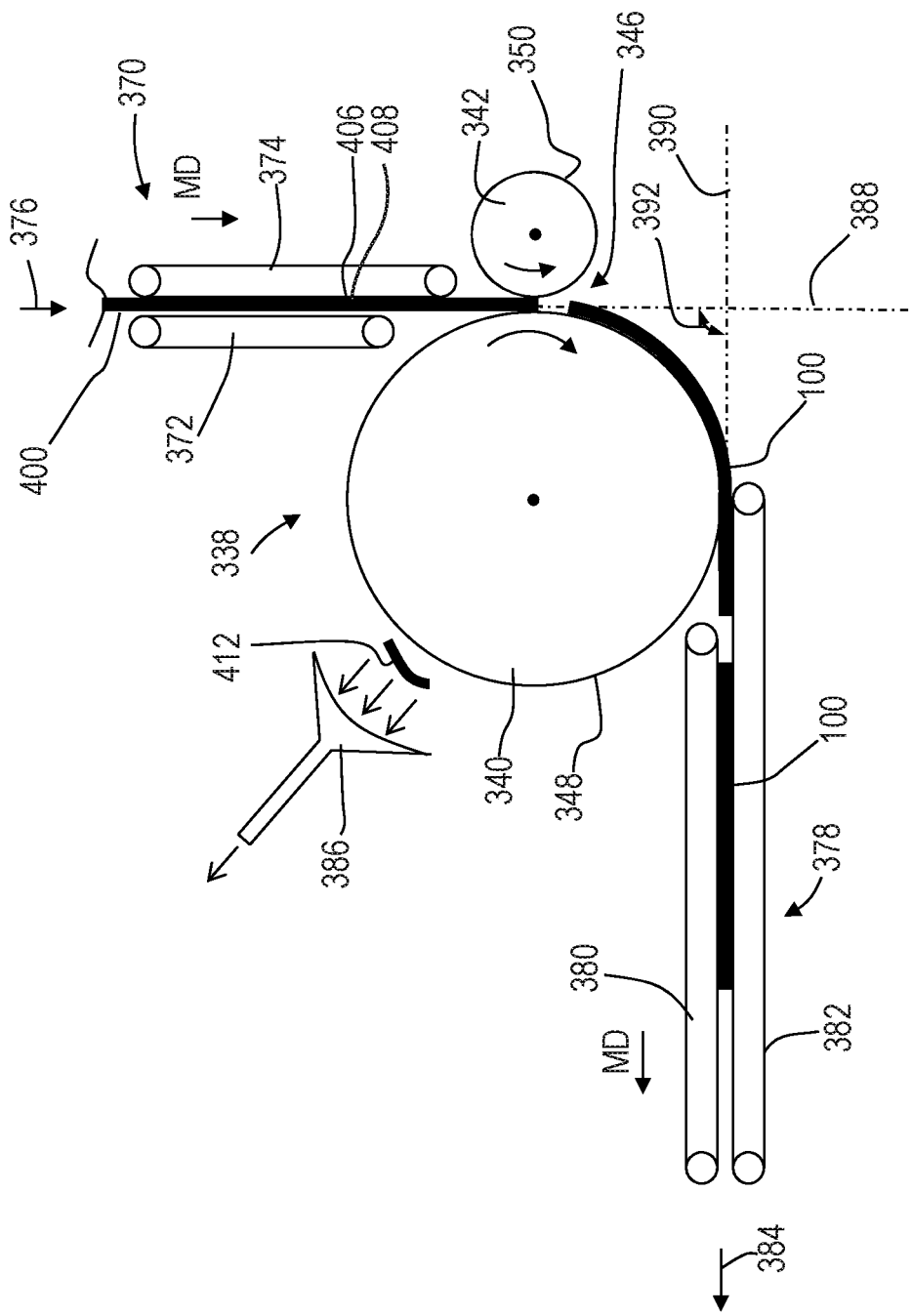
FIG. 8 is a schematic side view of a cutting apparatus.

As previously mentioned, the processes and apparatuses herein may also be configured in various ways to remove the pieces of trim material 412 from the cutting apparatus 338. In some configurations, the cutting apparatus 338 may be configured such that the pieces of trim material 412 are removed from an outer surface 348, 350 of the cutting roll 340 and/or anvil roll 342 after cutting discrete absorbent articles 100 from the continuous length of absorbent articles 400. For example, as shown in FIG. 8, a first carrier 370 advances a continuous length of absorbent articles 400 in a machine direction MD to the cutting apparatus 338. In particular, the first carrier 370 includes a first conveyor 372 and a second conveyor 374, and the continuous length of absorbent articles 400 is advanced in a first direction 376 between the first and second conveyors 372, 374 to the nip 346 between the knife roll 340 and the anvil roll 342. As discussed above, the cutting apparatus 338 simultaneously cuts the second belt laminate 408 and the first belt laminate 406 to form discrete absorbent articles 100 from the continuous length of absorbent articles 400 while also cutting pieces of trim material 412 to form contoured and/or shaped front and/or back elastic belts 106, 108 on the absorbent articles 100. The discrete absorbent articles 100 are then transferred from the cutting apparatus 338 to a second carrier 378. The second carrier 378 includes a first conveyor 380 and a second conveyor 382, and the discrete absorbent articles 100 are advanced in a second direction 384 between the first and second conveyors 380, 382 from the cutting apparatus 338.

The pieces of trim material 412 may be removed from the cutting apparatus after the cutting apparatus 338 cuts discrete absorbent articles 100 from the continuous length of absorbent articles 400. For example, as shown in FIG. 8, the pieces of trim material 412 may be temporarily held onto the outer circumferential surface 348 of the knife roll 340. As the knife roll 340 rotates, the trim material 412 is carried away from the nip 346 and may be transferred to a trim chute 386 adjacent the knife roll for subsequent disposal and/or recycling processes. It is to be appreciated that the knife roll 340 may be connected with a vacuum system to temporarily hold the trim material in position until the trim material 412 is transferred to the trim chute 386. In addition, the trim chute 386 may be connected with a vacuum system to help remove the trim material 412 from the knife roll 340.

As shown in FIG. 8, the cutting apparatus 338 may be configured such that the discrete absorbent articles are partially wrapped and held on the outer circumferential surface 348 of the knife roll 340 while advancing from the nip 346 to the second carrier 378. Holding the absorbent articles 100 in position on the outer surface 348 of the knife roll 340 after cutting may help prevent elastic materials that are cut under tension from retracting. Although the cutting apparatus 338 shown in FIG. 8 is configured to temporarily hold the trim material 412 and/or the discrete absorbent articles 100 on the knife roll 340, it is to be appreciated that the cutting apparatus 338 may configured to temporarily hold the trim material 412 and/or discrete absorbent articles 100 on the anvil roll 342.

With continued reference to FIG. 8, the advancement of the continuous length of absorbent articles 400 in the first direction 376 on the first carrier 370 defines a first article transport plane 388 along which the absorbent articles 400 are transported. And the advancement of the discrete absorbent articles 100 in the second direction 384 on the second carrier 378 defines a second article transport plane 390 along which the absorbent articles 100 are transported. It is to be appreciated that the first direction 376 and second direction 384 may be the same or different. As such, a transfer angle 392 may be defined by the intersection of the first and second transport planes 388, 390. It is to be appreciated that the first and second carriers may be aligned in various ways to define various sizes of transfer angles 392. For example, in some embodiments, the transfer angle 392 may be from 90 degrees to 180 degrees.

Although the cutting apparatus 338 may be configured to cut discrete absorbent articles 100 from the continuous length of absorbent articles 400 while at the same time forming contoured and/or shaped front and/or back elastic belts 106, 108 on the absorbent articles 100, it is to be appreciated that the process and apparatuses herein may be configured to perform these steps at different times. For example, the process may be configured with a separate trim removal unit forms the contoured and/or shaped front and/or back elastic belts 106, 108 on the absorbent articles 100 before cutting discrete absorbent articles 100 from the continuous length of absorbent articles 400. In some embodiments, the separate trim removal or contouring cut may be performed after the apparatus 334 operates to bond an overlap area 362, thus creating discrete bonds 336a, 336b. In other embodiments, the separate trim removal or contouring cut may be performed after the folding apparatus 332 folds the chassis also positions the wearer facing surface 312 of the second belt laminate 408 extending between each chassis 102 in a facing relationship with the wearer facing surface 312 of the first belt laminate 406 extending between each chassis 102, and before the apparatus 334 operates to bond an overlap area 362, thus creating discrete bonds 336a, 336b.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assembling disposable pant diapers, each pant diaper comprising a chassis having a first end region and an opposing second end region separated from each other by a central region, and having a longitudinal axis and a lateral axis, the chassis comprising: a topsheet, a backsheet, and an absorbent core disposed between the topsheet and the backsheet, the method comprising steps of:
   advancing a first continuous elastic laminate along a machine direction, the first continuous elastic laminate having an outer longitudinal edge and an inner longitudinal edge with a constant width, W1, in a cross direction;
   advancing a second continuous elastic laminate along the machine direction, the second continuous elastic laminate having an outer longitudinal edge and an inner longitudinal edge with a constant width, W2, in the cross direction;
   depositing a plurality of chassis spaced apart from each other along the machine direction onto the first continuous elastic laminate and the second continuous elastic laminate, wherein the first end regions of each chassis are connected with the first continuous elastic laminate, and the second end regions of each chassis are connected with the second continuous elastic laminate;
   folding each chassis along the lateral axis to position the first continuous elastic laminate into a facing relationship with the second continuous elastic laminate and forming uncovered regions of the second continuous elastic laminate intermittently spaced between the chassis along the machine direction and having a width, W3, extending in the cross direction formed by a distance extending between the inner longitudinal edge of the first continuous elastic laminate and the inner longitudinal edge of the second continuous elastic laminate;
   removing discrete pieces of trim material from the uncovered regions of the second continuous elastic laminate after the folding step; and
   cutting the first and second continuous elastic laminates in the cross direction to form discrete pant diapers.

2. The method of claim 1, further comprising a step of: advancing the first continuous elastic laminate in the facing relationship with the second continuous elastic laminate through a nip formed between a cutting roll and an anvil roll, wherein the cutting roll includes a blade having a distal edge extending in the cross direction and the machine direction; and
   wherein the steps of removing the discrete pieces of trim material and cutting the first and second continuous elastic laminates in the cross direction further comprise pressing the distal edge of the blade against the first continuous elastic laminate and the uncovered regions of the second continuous elastic laminate.

3. The method of claim 1, wherein the discrete pieces of the trim material each having a maximum width, TW, that is equal to the width, W3, of the uncovered regions.

4. The method of claim 1, wherein width, W2, of the second continuous elastic laminate is greater than the width, W1, of the first continuous elastic laminate.

5. The method of claim 1, further comprising steps of:
   advancing a first continuous substrate layer having a first surface and an opposing second surface in a machine direction, and a width in a cross direction;
   advancing a second continuous substrate layer having a first surface and an opposing second surface in a machine direction, and a width in a cross direction;
   advancing elastic strands in the machine direction;
   bonding the elastic strands between the first surface of the first substrate layer and the first surface of the second substrate layer to form an elastic laminate; and
   cutting the elastic laminate along the machine direction to form the first continuous elastic laminate and the second continuous elastic laminate.

6. The method of claim 5, wherein the step of bonding the elastic strands further comprises intermittently bonding the elastic strands in a stretched state between the first surface of the first substrate layer and the first surface of the second substrate layer such that the elastic laminate includes bonded regions and non-bonded regions intermittently spaced along the machine direction, wherein the elastic strands are bonded to the first surface of the first substrate layer and the first surface of the second substrate layer in the bonded regions, and wherein the elastic strands are not bonded to the first surface of the first substrate layer and the first surface of the second substrate layer in the non-bonded regions.

7. The method of claim 1, wherein the step of folding further comprises aligning the outer longitudinal edge of the first continuous elastic laminate with the outer longitudinal edge of the second continuous elastic laminate.

8. The method of claim 1, further comprising a step of bonding the first continuous elastic laminate with the second continuous elastic laminate at pairs of discrete bond regions separated from each other along the machine direction.

9. The method of claim 8, wherein the step of cutting the first and second continuous elastic laminates further comprises cutting the first and second continuous elastic laminates between pairs of discrete bond regions.

* * * * *